United States Patent
Shang

[19]

[11] Patent Number: 6,132,455
[45] Date of Patent: Oct. 17, 2000

[54] COOLING COMFORT SEAT CUSHION

[76] Inventor: Li-Jun Shang, No. 27 XiSan Huan North Road, Beijing, China, 100081

[21] Appl. No.: 09/245,466

[22] Filed: Feb. 5, 1999

[51] Int. Cl.[7] .............................. A61F 7/00; A47C 20/02
[52] U.S. Cl. ............................. 607/108; 607/96; 5/654; 5/655.5
[58] Field of Search .................. 607/96, 108; 5/421, 5/654, 655.5

[56] References Cited

U.S. PATENT DOCUMENTS

| | | |
|---|---|---|
| 4,287,076 | 9/1981 | Babin et al. . |
| 4,292,189 | 9/1981 | Chen . |
| 4,508,632 | 4/1985 | Takeda et al. . |
| 4,671,267 | 6/1987 | Stout . |
| 4,964,402 | 10/1990 | Grim et al. . |
| 5,456,852 | 10/1995 | Isiguro . |
| 5,681,298 | 10/1997 | Brunner et al. ............ 604/361 |

*Primary Examiner*—Linda C. M. Dvorak
*Assistant Examiner*—Jocelyn Debra Ram

[57] ABSTRACT

The present invention comprises a thin layer of a cooling composition having a novel and narrow relative range of components, where such thin layer is maintained as such in a thin sheath for use as a cooling cushion especially for the seat of a sitting human, but may also be used for the back of a reclining human. The use of this cushion is for ambient temperatures at about 75.3° F. (23° C.) and above, i.e., the initial melting temperature for the cooling composition incorporating a specific phase change material.

4 Claims, 1 Drawing Sheet

COOLING COMFORT SEAT CUSHION

BACKGROUND OF THE INVENTION

The present invention relates to seat and back cushions for humans, especially those providing both a cooling function and continuously fluidized coolant material throughout the temperature range in which the cushions will be used.

U.S. Pat. No. 4,508,632 describes a heat storage material which comprises a mixture of sodium sulfate decahydrate or sodium thiosulfate pentahydrate, and urea. The mixing ratio by mole of the sulfate decahydrate to urea is in the range of 1:1 to 1:3 and the mixing ratio by mole of the thiosulfate pentahydrate to urea is in the range of 1:2 to 1:8.

U.S. Pat. No. 4,292,189 describes a thermal energy storage composition that stores heat upon melting and releases heat upon solidification. It is composed of a mixture of sodium sulfate decahydrate, sodium carbonate decahydrate, sodium borate decahydrate and a thickening agent. Its good heat transfer characteristics, relatively high latent heat of fusion, low cost, and favorable melting point allow this material to be particularly useful for space heating applications.

U.S. Pat. No. 4,287,076 describes a method for the storage and conveyance of thermal energy at low temperature, by using the latent heat produced by a substance during changes of state. This substance consists of a salt producing considerable latent heat during change of state, such as Na2SO4.10H2O, combined closely with a nucleating agent such as borax and dispersed in an oil to which an emulsifying agent has been added. This product is particularly suitable for storage of solar energy at low temperature and for heating of enclosed areas.

U.S. Pat. No. 4,964,402 describes an orthopedic device for treatment of injured joints or limbs having at least one gel pad including at least one phase change material for improving the thermal energy storage capacity of the gel pad. The phase change material included in the gel material inside the gel pad may be encapsulated, formed in pellets, soluble, insoluble, or in any desirable form. The gel pad may be removed from the orthopedic device, heated or cooled, and then used with the device for hot or cold therapy of injured joints or limbs, taking advantage of the increased thermal energy storage capacity of the phase change material. Two different phase change materials may be included in the gel pad, one of which may be used for cold temperature therapy while the other is used for hot temperature therapy. The gel pad may include encapsulated water as a phase change material. In addition, a sheet of encapsulated phase change material may be used inside the gel pad which prevents the phase change material from moving inside the gel pad in order to provide a uniform distribution of phase change material inside the pad, resulting in uniform temperature distribution for hot or cold therapy.

U.S. Pat. No. 5,456,852 describes a microcapsule for heat-storing material which encapsulates a compound capable of undergoing phase transitions, said microcapsule containing a high-melting compound having a melting point 20°–110° C. higher than that of the compound capable of undergoing phase transitions.

U.S. Pat. No. 4,671,267 describes the use of a pliable, self-sustaining, moisture sorbing gel including a humectant such as glycerin entrapped within a synthetic resin polymer matrix (e.g., a matrix containing acrylic acid or acrylamide monomer moieties). In one preferred embodiment, a body of the gel is encased within heat and moisture-permeable stretch fabric, and securing ties or the like are provided to permit the composite to be conformed to a body part and held in place. In use, such therapy wraps are either heated (as in a microwave oven) or refrigerated, so as to provide appropriate thermal treatment; it has been found that the preferred gel of the invention retains its pliability and other physical properties over a very broad temperature range, such as −20° to 305° F., and therefore the wraps of the invention can be used in many treatment contexts. It has also been discovered that the gel material can be applied directly to injured skin to in effect create a temporary skin with ideal air permeability. Furthermore, the moisture absorbing and desorbing properties of the gel create a moisture equilibrium between the gel, damaged skin and the atmosphere, thus promoting rapid healing.

The following table comprises some common materials whose solid—liquid phase transition temperature ranges have been found to have application in direct or sheathed contact with human skin for one or more uses:

| Phase Change Material | Type | MP (° C.) |
| --- | --- | --- |
| MgCl2.6H2O | Quasicongruent | 117 |
| Mg(NO3).6H2O | Congruent | 89 |
| Na4P2O7.10H2O | Incongruent | 70 |
| NaOAc.3H2O | Incongruent | 58 |
| MgCl2.6H2O/Mg(NO3)2.6H2O | Eutectic | 58 |
| Paraffin wax | Congruent | 50 |
| Na2S2O3.5H2O | Semicongruent | 48 |
| Neopentyl glycol | Congruent | 43 |
| CaBr2.6H2O | Congruent | 34 |
| Na2SO4.10H2O | Incongruent | 32 |
| CaCl2.6H2O | Semicongruent | 28 |
| Polyethylene glycol | Congruent | 23 |
| Na2SO4.10H2O/NaCl | Incongruent | 18 |
| CaBr2.6H2O/CaCl2.6H2O | Isomorphous | 15 |
| Na2SO4.10H2O/KCL/NH4Cl | Incongruent | 8 |

Na2SO4.10H2O is not associated with uses for cooling upon consideration of its melting temperature just under the normal temperature for humans. Such a phase change material is considered in the prior art to have mostly use in the area of heat treatment gel pads applied to the skin surface.

SUMMARY OF THE INVENTION

The present invention comprises a thin layer of a cooling composition having a novel and narrow relative range of components, where such thin layer is maintained as such in a thin sheath for use as a cooling cushion especially for the seat of a sitting human, but may also be used for the back of a reclining human. The use of this cushion is for ambient temperatures at about 75.3° F. (23° C.) and above, i.e., the initial melting temperature for the cooling composition incorporating a specific phase change material. It has been surprisingly found that the generation of heat by the seated or reclining person raises the interface temperature between the person and the cushion surface to above the melting temperature of sodium sulfate decahydrate as used in the cooling composition while maintaining for a comfortable cushion/person interface temperature for the seated or reclining person. Thus, the use of sodium sulfate decahydrate as a phase change material in the application of the composition of the present invention for the purpose of providing a cooling, as contrasted to a heating or heat retaining use, has heretofore been unknown to the prior art.

The present invention composition provides a particularly effective fluidized material even at temperatures below about 10° F., providing comfort, shock and seat-projection protecting functions for the seated or reclining person. The solid phase crystals of the sodium sulfate decahydrate at below its melting temperature in the invention composition are less than about 1–2 millimeters in diameter and are maintained at sufficient distance from each other in the gel matrix of the invention composition to provide a comfortable and fluidized cushion for the seated or reclining person regardless of the ambient temperature.

It has been found that a particular cushion/person interface comfort range for the seated or reclining person is about 85°–95° F. Although this may have been known in the prior art, the application of the present cooling composition has not heretofore been known. The melting point of sodium sulfate decahydrate at about 89° F. has made it an ideal material in the present invention for maintaining a comfortable cushion/person interface temperature of about 90°–95° F. without creating an uncomfortably cold surface, as may be appreciated if a person is seated on a heat sink surface maintained at about 80° F. or cooler for a substantial period of time. The cushion of the present invention would, even after a very long period of contact with a seated or reclining person, feel neither warm or cool, although the heat sink effect of the solid to liquid phase transition of the high relative amounts of sodium sulfate decahydrate makes this invention in effect a cooling cushion as it absorbs body heat to maintain a comfortable temperature.

In addition, the present invention provides a phase change material that is easily re-solidified at typical ambient temperatures, i.e., any ambient temperature below about 86° F., but more preferably about 75° F., will cause the phase change material to re-solidify, making the cooling cushion immediately renewable for the seated or reclining person without having to find a refrigeration source, as is necessary for prior art cooling gel pads.

DETAILED DESCRIPTION OF THE INVENTION

The phase change material sodium sulfate decahydrate is maintained in a gel with substantial capacity for maintaining the formed and re-formed crystals of sodium sulfate decahydrate in a fluid matrix at substantially even distances from each other as the phase change material melts and re-solidifies. The ranges for the components comprising the gel and phase change material are as follows:

| Component | Relative Parts by Weight |
| --- | --- |
| $Na_2SO_4.10H_2O$ | 87.5 |
| Surfactant | 0.8 |
| Ethylene Glycol | 7.3 |
| Acrylic Acid Resin | 0.7 |
| Nucleating Agent | 3.7 |

It has been found that, except for sodium sulfate decahydrate, the substantial benefit of the present invention is provided by the above components in the relative amounts as just specifically described within a range of ±15% from the specific values. For sodium sulfate decahydrate, the substantial benefit of the present invention is provided by the above components in the relative amounts as just specifically described within a range of 87.5 to about 70 from the specific value. Preparation of the above composition is made in the following manner. Thirty-one parts by weight $Na_2SO_4$ are dissolved in 56.5 parts by weight $H_2O$ at 50–60° C. Maintaining the dissolved $Na_2SO_4.10H_2O$ at least well above the melting point of the material, 0.8 parts by weight surfactant (C12 to C16 alkyl sulfonate sodium salt or C12 to C16 alkyl benzyl sulfonate sodium salt), 7.3 parts by weight of ethylene glycol, and 0.7 parts by weight acrylic acid resin are added to the molten material and agitated until a visible emulsion is formed. At that point, 3.7 parts by weight of $Na_2B_4O_4.10H_2O$ or NaCl are added as a nucleating agent. The combination of specific amounts of the surfactant, ethylene glycol, acrylic acid resin (alkyl, i.e., methyl, ethyl or butyl, benzyl or their effective equivalents) and nucleating agent produces a composition high in phase change material and yet, at temperatures below the melting temperature of $Na_2SO_4.10H_2O$, still fluidized, shock absorbent and conformable to the human seat and back on normal sitting or reclining pressure.

The cooling composition material containing phase change material is encapsulated inside a thin film of vinyl, urethane, copolymer latex of butadiene-acrylonitrile, copolymer of vinylidene chloride-acrylic, resinous latex, rubber latexes, epoxy polymers, polyurethane polymers, acrylic polymers, cellulose acetate, polyamides, any resin, or the like. The cooling material composition makes it essentially non-reactive with most flexible polymer sheeting material that may be effectively sealed to be adapted to present a cushion/person interface covering and encapsulating relatively thin fluidized layer of cooling composition material. The gel matrix for the phase change material requires a liquid tight seal be made between the environment and the cooling composition material.

Figure 1:
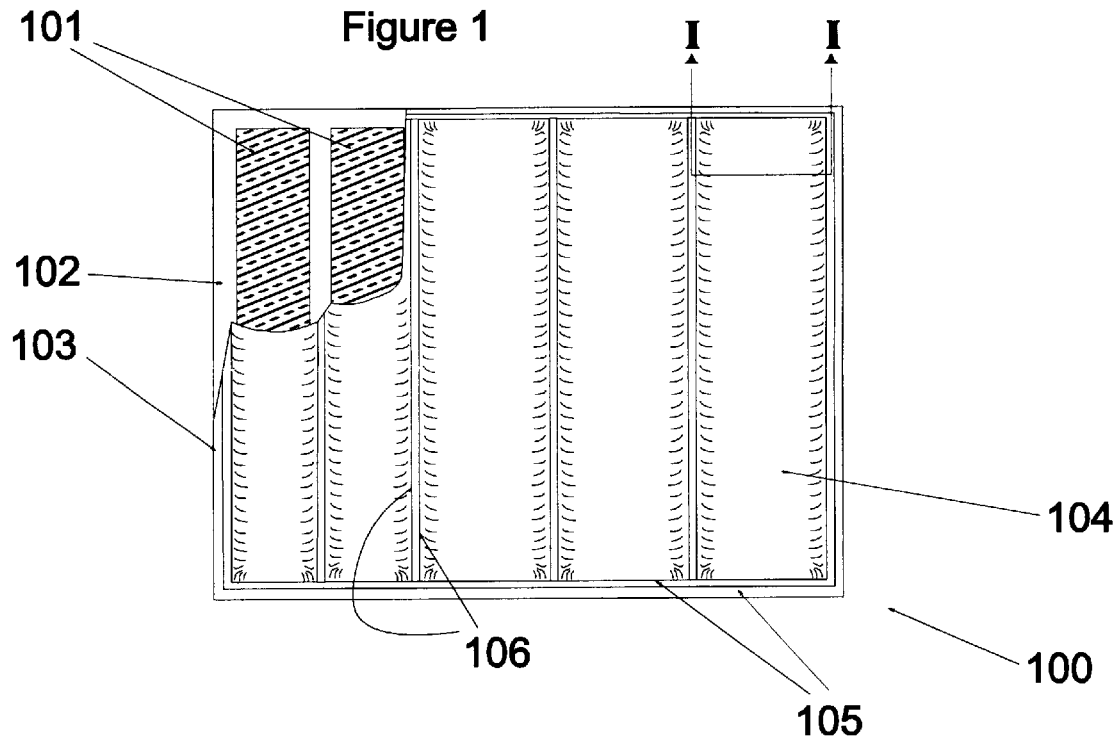
FIG. 1 is a top, partially cut away, view of a seat cushion of the present invention with five parallel sheathed envelopes, each envelope enclosing a thin layer of the cooling composition material of the present invention.
Figure 2:
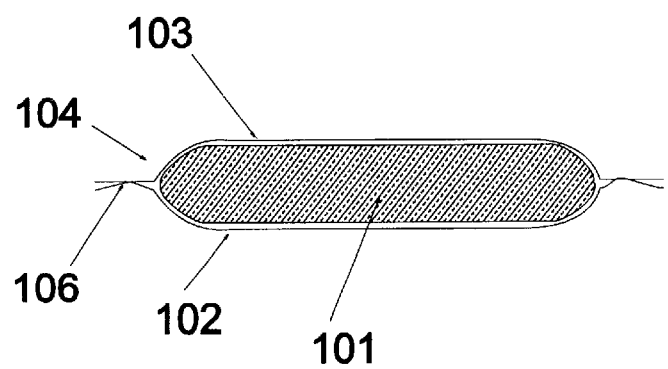
FIG. 2 is a cross section A—A of one of the envelopes of the seat cushion of FIG. 1.

FIG. 1 shows a simple preferred embodiment for a cooling cushion 100 for the seat of a seated person as in the present invention, comprising five parallel envelopes 104 of flexible sheeting material heat sealed against each other and the environment. Each envelope 104 is comprised of a top sheet 103 and bottom sheet 102 and holds about 0.7 kg of cooling composition material 101 in a layer preferably about 3–25 millimeters thick, more preferably about 5–15 millimeters thick, with a length of 350–450 millimeters and a width of about 50–75 millimeters. The heat sealed seams 105 and 106 and extra material required for it as between are illustrative only, however it is preferred that the inter-envelope distance be reduced as much as possible to improve heat transfer to the cooling composition material through the flexible sheeting material. FIG. 2 shows a cross-section of one of the envelopes of cooling composition material in FIG. 1.

The present invention may be used in almost any seating or reclining device in which a human may rest where a seating or reclining device surface/person interface is formed where the person may generate sufficiently high (above about 95° F.) interface temperatures to feel uncomfortable or perspire. The cushion of the present invention, although not a permanent relief from such discomfort, can maintain the interface temperature at or below a discomfort or perspiration temperature for up to or more than an hour at a time. The size and configuration of an individual cushion or envelope in such a cushion will be easily adaptable to one skilled in the art of forming cushions for such devices, except that it is preferred to maintain the preferred thickness of cooling composition material in an envelope with no greater than about 75 millimeter width from sealed seam to sealed seam so that the cooling composition material is not pressured to a pocket toward one of the seams and reduce the effectiveness of the less thick zone of cooling composition material at the other seam.

In addition, the cushion of the present invention, although presenting the potential wearer with a substantial amount of weight, may have a cushion of various sizes incorporated into clothing to maintain a comfortable temperature for the wearer.

In another embodiment of the present invention, the cooling composition may incorporate menthol (borneal mint), lemon or other such pleasant scents to heighten the impression of comfort for the person in heat transfer contact with the cooling cushion of the present invention.

The above design disclosures present the skilled person with considerable and wide ranges from which to choose appropriate obvious modifications for the above examples. However, the objects of the present invention will still be obtained by the skilled person applying such design disclosures in an appropriate manner.

I claim:

1. A cooling cushion comprising:

(a) a flexible sheeting material encapsulating a cooling composition material; and (b) the cooling composition material comprising the following components:

| Component | Wt. % Range in Composition |
|---|---|
| Na2SO4.10H2O | 87.5 to 70 |
| Surfactant | 0.8 to 15% |
| Ethylene Glycol | 7.3 to 15% |
| Acrylic Acid Resin | 0.7 to 15% |
| Nucleating Agent | 3.7 to 15% | whereby the surfactant, ethylene glycol, and acrylic acid resin are added to molten Na2SO4.10H2O and agitated until a visible emulsion is formed, whereafter, the nucleating agent is added and mixed to uniformity, the resulting material forming the cooling composition material.

2. The cushion of claim 1 wherein the flexible sheeting material is adapted to provide encapsulation of the cooling composition material to form a body such that the body thickness is from about 3–25 millimeters and may be held against a person such that a cushion/person interface is formed whereby substantial heat transfer may occur from a seated or reclining person to the cooling composition material to maintain comfort for that person.

3. The cushion of claim 2 wherein the flexible sheeting material forms an encapsulating envelope permitting a width of the body less than about 75 millimeters.

4. The cushion of claim 1 wherein the body has a thickness of about from 5–15 millimeters and is adapted such that for substantial time the temperature of the cushion/person interface is maintained at about 95° F. or less.

* * * * *

UNITED STATES PATENT AND TRADEMARK OFFICE
CERTIFICATE OF CORRECTION

PATENT NO. : 6,132,455

DATED : October 17, 2000

INVENTOR(S) :.LI-JUN SHANG

It is certified that error appears in the above-identified patent and that said Letters Patent is hereby corrected as shown below:

ON THE TITLE PAGE

Item [75] Inventor address should read –1506 1$^{st}$ District, Anzhangi Li, Beijing, China, 10029 --.

Signed and Sealed this

Eighth Day of May, 2001

*Attest:*

NICHOLAS P. GODICI

*Attesting Officer*    *Acting Director of the United States Patent and Trademark Office*